United States Patent
Zefirov et al.

(10) Patent No.: US 7,071,206 B2
(45) Date of Patent: *Jul. 4, 2006

(54) AGENTS FOR TREATING NEURODEGENERATIVE DISORDERS

(75) Inventors: Nikolai S. Zefirov, Moscow (RU); Andrei Z. Afanasiev, Chernogolovka (RU); Svetlana V. Afanasieva, Chernogolovka (RU); Sergei O. Bachurin, Chernogolovka (RU); Sergei E. Tkachenko, Chernogolovka (RU); Vladmir V. Grigoriev, Chernogolovka (RU); Marina A. Jurovskaya, Moscow (RU); Valery P. Chetverikov, Novokuznetsk (RU); Elizaveta E. Bukatina, Moscow (RU); Irina V. Grigorieva, Moscow (RU)

(73) Assignee: Medivation, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/004,001

(22) Filed: Dec. 2, 2004

(65) Prior Publication Data

US 2005/0096342 A1    May 5, 2005

Related U.S. Application Data

(63) Continuation of application No. 10/652,435, filed on Aug. 28, 2003, now abandoned, which is a continuation of application No. 10/057,688, filed on Jan. 23, 2002, now abandoned, which is a continuation of application No. 09/778,662, filed on Feb. 6, 2001, now abandoned, which is a continuation of application No. 09/269,602, filed as application No. PCT/RU96/00306 on Oct. 23, 1996, now Pat. No. 6,187,785.

(30) Foreign Application Priority Data

Oct. 23, 1995 (RU) .................................. 95118252

(51) Int. Cl.
*A61K 31/44* (2006.01)

(52) U.S. Cl. ..................................................... 514/292
(58) Field of Classification Search ................. 514/292
See application file for complete search history.

(56) References Cited

U.S. PATENT DOCUMENTS

| | | | |
|---|---|---|---|
| 3,718,657 A | 2/1973 | Garmaise et al. | |
| 3,743,740 A | 7/1973 | Barkov et al. | |
| 3,991,199 A * | 11/1976 | Berger | 514/292 |
| 4,636,563 A | 1/1987 | Abou-Gharbia | |
| 4,985,256 A | 1/1991 | Glick | |
| 5,319,096 A * | 6/1994 | Kosley et al. | 548/483 |
| 5,958,919 A | 9/1999 | Olney et al. | |
| RE36,397 E | 11/1999 | Zhang et al. | |
| 6,017,957 A | 1/2000 | Skolnick et al. | |
| 6,187,785 B1 * | 2/2001 | Zefirov et al. | 514/292 |
| 6,362,160 B1 | 3/2002 | Dawson et al. | |
| 6,391,871 B1 | 5/2002 | Olney et al. | |
| 6,930,112 B1 | 8/2005 | Weaver et al. | |
| 2001/0020028 A1 | 9/2001 | Zefirov et al. | |
| 2002/0102597 A1 | 8/2002 | Bitler et al. | |
| 2002/0115682 A1 | 8/2002 | Zefirov et al. | |
| 2002/0197233 A1 | 12/2002 | Relton et al. | |
| 2004/0044022 A1 | 3/2004 | Zefirov, Jr. et al. | |

FOREIGN PATENT DOCUMENTS

| | | |
|---|---|---|
| CA | 2 117 755 | 10/1993 |
| DE | 1952800 | 10/1969 |
| DE | 1813229 | 8/1970 |
| EP | 0 230 370 A2 | 7/1987 |
| EP | 0 230 370 A3 | 7/1987 |
| EP | 0 230 370 B1 | 7/1987 |
| EP | 0 424 179 A2 | 4/1991 |
| EP | 0 424 179 A3 | 4/1991 |
| EP | 0 581 456 A1 | 2/1994 |
| GB | 1245155 | 9/1971 |
| GB | 1276113 | 6/1972 |
| GB | 1450002 * | 9/1976 |
| GB | 1586655 * | 3/1981 |
| JP | 9-216882 | 8/1997 |

(Continued)

OTHER PUBLICATIONS

Enlglish Language Equivalent Abstract of SU 873883, which is GB 1,586,655.*

(Continued)

*Primary Examiner*—Dwayne Jones
(74) *Attorney, Agent, or Firm*—Morrison & Foerster LLP

(57) ABSTRACT

Compounds and methods of using these compounds to treat neurodegenerative diseases, especially Alzheimer's disease, are provided. The compounds that are provided for the treatment of neurodegenerative diseases can be represented by a general formula (I):

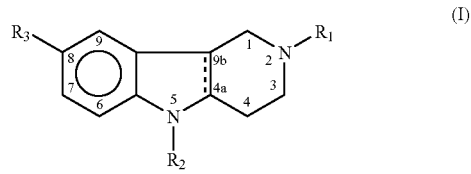

wherein $R_1$ is Me, Et or $PhCH_2$; $R_2$ is H, $PhCH_2$ or 6-Me-3-Py-$(CH_2)_2$; and $R_3$ is H, Me or Br. The solid line accompanied by the dotted line i.e.

----- represents a single or double bond and salts thereof with pharmacologically acceptable acids and quaternary derivatives.

13 Claims, No Drawings

FOREIGN PATENT DOCUMENTS

| RU | 2 106 864 C1 | 3/1998 |
|---|---|---|
| RU | 2 140 417 C1 | 10/1999 |
| SU | 1138164 A | 2/1985 |
| SU | 1803108 A1 | 3/1993 |
| SU | 1816451 A1 | 5/1993 |
| WO | WO-94/06428 A1 | 3/1994 |
| WO | WO-97/15225 A1 | 5/1997 |
| WO | WO-2005/055951 A2 | 6/2005 |

OTHER PUBLICATIONS

Enlglish Language Equivalent Abstract of SU 592359, which is GB 1,450,002.*
Enlglish Language Equivalent Abstract of SU 665804, which is US 3,991,199.*
Abou-Gharbia, M. et al. (1987). "Antipsychotic Activity of Substituted y-Carbolines," *J. Med. Chem.* 30:1818-1823.
Avdulov, N.A. et al. (1985). "Interaction of Psychotropic Preparations with Model Lipid Membranes," *Bulletin of Experimental Biology and Medicine* 100(10):440-442. (English Translation, 4 pages.).
Baker, G.T. (Jan.-Apr. 1993). "Effects of Various Antioxidants on Aging in *Drosophila,*" *Toxicol. Ind. Health* 9(1/2):163-186.
Benes, L. (1986). "Free Radicals and Ischemic States," *Ceskoslovenska Farmacie* 35(5):230-232. (English Translation, 5 pages.).
Benes, L. (Jun. 1986). "Free Radicals and Ischemic States," *The Czechoslovak Pharmcy Journal* 35(5):230-232. (Alternative English Translation, 5 pages.).
Bukatina, Y.Y. et al. (1992). "Scale For Evaluating the Mental Condition of Elderly Dementia Patients," *Social and Clinical Psychiatry* 2(4):29-37. (English Translation, 10 pgs.).
Buu-Hoï, N.P. et al. (1964). "Carcinogenic Nitrogen Compounds. Part XXXIX. A New Synthesis of y-Carbolines and 2,10-Diaza-anthracenes," *J. Chem. Soc.* 2:708-711.
Cattanach, C.J. et al. (1968). "Studies in the Indole Series. Part IV. Tetrahydro-1$H$-pyrido[4,3-b]-indoles as Serotonin Antagonists," *J. Chem. Soc.* C:1235-1243.
Collingridge, G.L. et al. (1994). *The NMDA Receptor* Second Edition, Oxford University Press: New York, NY, 4 pages (Table of Contents Only.).
Comfort, A. et al. (Jan. 22, 1971). "Effect of Ethoxyquin on the Longevity of C3H Mice," *Nature* 229(5282):254-255.
Disterhoft, J.F. et al. eds. (Dec. 15, 1994). "Calcium Hypothesis of Aging and Dementia," *Ann. N.Y. Acad. Sci.* vol. 747, 6 pages. (Table of Contents Only.).
Evans, R.H. et al. (Jan. 1982). "The Effects of a Series of ω-Phosphonic α-Carboxylic Amino Acids on Electrically Evoked and Excitant Amino Acid-Induced Responses in Isolated Spinal Cord Preparations," *Brit. J. Pharmacol.* 75:65-75.
Frolkis, V.V. et al. (1991). *Life Span Prolongation*, Translated from Russian by Edelsburg, N.G., CRC Press: Boca Raton, FL, 9 pages, including Table of Contents.
Gankina, Y.M. et al. (1992). "Effect of Certain Antihistamine Preparations on $^3$H-Mepyramine and $^3$H-Cimetidine Binding to Histamine Receptors in the Rat Brain," *Chemical and Pharmaceutical Journal* 26(5):9-12. (English Translation, 5 pages.).
Gankina, Y.M. et al. (1993). "Effect of Antihistamine Preparations on Labeled Mepyramine, Ketanserin, and Quinuclidinyl Benzilate Binding in the Rat Brain," *Experimental and Clinical Pharmacology* 56(1):22-24. (English Translation, 5 pages.).

Geerts, H. et al. (2003). "Galantamine Benefits in Alzheimer's Disease are Related to Increases in Dopamine Output," *Abstracts of the IX International Congress on Schizophrenia Research*, Colorado Springs, CO, Mar. 29-Apr. 2, 2003, 60(1):135.
Gill, R. et al. (1987). "High-Performance Liquid Chromatographic System for the Separation of Tricyclic Antidepressant and Related Drugs Using ODS-Hypersil," *Journal of Chromatography* 391(2):461-464.
Grigoryev, V.V. (1993). "Effects of NMDA and Quinolinic Acid on Rat Cerebral Cortex Neurons," *Reports From the Academy of Sciences* 330(5):646-648. (English Translation, 4 pgs.)
Grigoryev, V.V. et al. (1988). "Anticonvulsant Activity of Glutamate Receptor Antagonists in the Phosphorus-Containing Aminocarboxylic-Acid Series," *J. of Chem. and Pharm.* 22(3):275-277. (English Translation, 3 pgs.).
Harbert, C.A. et al. (1980). "Neuroleptic Activity of the 5-Aryltetrahydro-y-carboline Series," *Mol. Pharm.* 17(1):38-42.
Heller, W.M. et al. eds. (1989). *USAN and the USP Dictionary of Drug Names: USAN 1990: 1961-1989 Cumulative List*, U.S. Pharmacopeial Convention, Inc.: Rockville, MD, 26th edition, p. 196.
Hörtein, U. (1954). "On Knowledge of the Tetrahydrocarboline Compounds (Communication I)," *Chem. Ber.* 87(4):463-472. (English Translation, 13 pgs.).
Kittová, M. et al. (Nov. 1985). "Antiarrhythmic and Hemodynamic Effects of a Pyridoindole Derivative (DH 1011) on Experimental Models of Heart Rhythm and Function Disorders," *Bratisl Lek. Listy.* 84(5):542-556. (English Translation, 15 pages.).
Klyuyev, M.A. ed. (1991). *Handbook: Medicinal Agents Used in Medical Practice in the USSR* Meditsina Publishing House: Moscow, USSR, p. 512. (English Translation, 2 pgs.).
Koh, J-Y. et al. (1990). "β-Amyloid Protein Increases the Vulnerability of Cultured Cortical Neurons to Excitotoxic Damage," *Brain Res.* 533:315-320.
Kost, A.N. et al. (1973). "Indole Chemistry: XXXIII. On NH Group Pyridylethylation in Indole Compounds," *Heterocyclic Compound Chemistry* 2:207-212. (English Translation, 6 pgs.).
Kucherova, N.F. et al. (1956). "Indole Derivatives. II. Synthesis of Certain 1,2,3,4-Tetrahydro-y-Carboline Derivatives," *J. of General Chemistry* 26(88):3149-3154. (English Translation, 6 pages.).
Lal, H. et al. eds. (1989). *Excitatory Amino Acids and Drug Research*, Alan R. Liss, Inc.: New York, NY, 17(4):380.
Litchfield, J.T. Jr. et al. (1949). "A Simplified Method of Evaluating Dose-Effect Experiments," *J. Pharmacol. Exp. Therap.* 96:99-113.
Maragos, W.F. et al. (Mar. 9, 1987). "Loss of Hippocampal [$^3$H]TCP Binding in Alzheimer's Disease," *Neurosci. Lett.* 74(3):371-376.
Mashkovskiy, M.D. (1993). *Drugs: (A Manual for Physicians)*, Meditsina Publishing House: Moscow, USSR, 12th Edition, 1:383. (English Translation, 4 pages.).
Mattson, M.P. (Jan. 1990). "Antigenic Changes Similar to Those Seen in Neurofibrillary Tangles are Elicited by Glutamate and Ca$^{2+}$Influx in Cultured Hippocampal Neurons," *Neuron* 2:105-117.

Mattson, M.P. et al. (Feb. 1992). "β-Amyloid Peptides Destabilize Calcium Homeostasis and Render Human Cortical Neurons Vulnerable to Excitotoxicity," *J. Neurosci.* 12(2):376-389.

Melkumova, Y.R. (1994). "Antianginal and Antifibrillatory Properties of Dimebon," *Dissertation: Kuban State Medical Academy,* 170 pgs. (English Translation of section 5.1-5.4, 8 pages.).

Mills, L.R. et al. (Jan. 1990). "Neuron-Specific and State-Specific Differences in Calcium Homeostatis Regulate the Generation and Degeneration of Neuronal Architecture," *Neuron* 2:149-163.

Murray, A.M. et al. (1991). "Disturbances in Pre- and Postsynaptic Dopamine Systems in Parkinson's and Alzheimer's Disease," *Abstracts: Society for Neuroscience, 21st Annual Meeting of the Society for Neuroscience*, New Orleans, LA, Nov. 10-15, 1991, 17(2):1260. Abstract 499.7.

Obukhova, L.K. (1975). "Chemical Geroprotectors and the Problem of Increasing Lifespan," *Uspekhi Khimii* (Russ.) 44:1914-1925. (English Translation, 19 pages.).

Prelli, F. et al. (Aug. 1988). "Differences Between Vascular and Plaque Core Amyloid in Alzheimer's Disease," *J. Neurochem.* 51(2):648-651.

Saitoh, T. et al. (May 1991). "Protein Kinases and Phosphorylation in Neurologic Disorders and Cell Death," *Lab Invest.* 64(5):596-616.

Shadurskaya, S.K. et al. (1986). "Neuromediator Mechanisms of the Effects of the Antihistamine Preparation Dimebon on the Brain," *Bulletin of Experimental Biology and Medicine* S1(6):700-702. (English Translation, 4 pages.).

Stolc, S. et al. (1995). "Protective Effect of Stobadine, a Pyridoindole Antioxidant, in Hypoxia-Reoxygenation Injury of Ganglionic and Hippocampal Neurotransmission," *Molecular and Chemical Neuropathology* 25:199-212.

Tishchenkova, I.F. et al. (1991). "Detection of Dimebon in Biological Fluids and Tissue Homogenates Using the Thin-Layer Chromatography Densitometry Technique," *J. of Chem. and Pharm.* 25(11):78-79. (English Translation, 4 pgs.).

Volger, B.W. (Jun. 1991). "Alternatives in the Treatment of Memory Loss in Patients with Alzheimer's Disease," *Clinical Pharmacy* 10(6):447-456.

Welch, W.M. et al. (1986). "Neuroleptics from the 4a,9b-*cis*- and 4a,9b-*trans*-2,3,4,4a,5,9b-Hexahydro-1*H*-pyrido[4,3-b]indole Series. 2," *J. Med. Chem.* 29:2093-2099.

Wolfe, N. et al. (Jan. 1988). "Neuropsychological Deficits Linked to Dopamine Deficiency in Alzheimer's Disease, Parkinson's Disease and Major Depression," *Journal of Clinical and Experimental Neuropsychology* 10(1):33.

Yakhontov, L.N. et al. (1983). *Synthetic Drugs* Natradze, A.G. ed., Meditsina Publishing House: Moscow, USSR, pp. 234-237 and Table of Contents (English Translation, 7 pages.).

Yankner, B.A. et al. (Oct. 12, 1990). "Neurotrophic and Neurotoxic Effects of Amyloid β Protein: Reversal by Tachykinin Neuropeptides," *Science* 250(4978):279-282.

Yurovskaya, M.A. et al. (1981). "Interaction of 1,2,3,4-Tetrahydro-γ-Carboline Iodomethylates with Nucleophilic Agents," *Heterocyclic Compound Chemistry* 8:1072-1078. (English Translation, 7 pgs.).

Anonymous. (1984). Table 78 In Early Diagnostics of Metabolic Diseases, Moscow, Russia, p. 304. (English Translation, 4 pages).

Benes, L. (Jun. 1986). "Free Radicals and Ischemic States," *Ceskoslovenska Farmacie* 35(5):230-232. (Abstract Only.).

Obukhova, L.K. et al. (1984). "Molecular Mechanisms of Aging Retardation by Antioxidants," *Biological Problems of Aging* (Russ.) 4:44-80. (English Translation, 46 pages.).

* cited by examiner

AGENTS FOR TREATING NEURODEGENERATIVE DISORDERS

CROSS REFERENCE TO RELATED APPLICATIONS

This application is a continuation of U.S. patent application Ser. No. 10/652,435, filed on Aug. 28, 2003 now abandoned, which is a continuation of U.S. patent application Ser. No. 10/057,688, filed on Jan. 23, 2002, now abandoned, which is a continuation of U.S. patent application Ser. No. 09/778,662, filed on Feb. 6, 2001, now abandoned, which is a continuation of U.S. patent application Ser. No. 09/269,602, filed on Mar. 25, 1999, which issued as U.S. Pat. No. 6,187,785 on Feb. 13, 2001, which claims priority under 35 U.S.C. 371 to PCT Application No. PCT/RU96/00306, filed on Oct. 23, 1996, which claims priority to Russian Federation Application No. 95118252, filed Oct. 23, 1995, the disclosures of each of which are hereby incorporated herein by reference.

BACKGROUND OF THE INVENTION

1. Field of the Invention

The present invention relates to the use of chemical compounds in medicine, more specifically, to the use of the compounds selected from hydrogenated pyrido[4,3-b]indoles for the treatment of neurodegenerative diseases, and especially Alzheimer's disease (AD), due to the discovery of new properties intrinsic to these compounds.

2. Description of the Related Art

Alzheimer's disease is currently one of the severest and widely spread neurodegenerative diseases. The most traditional approach to the treatment of this disease is compensatory therapy based on the compensation of the cholinergic system functions which are reduced in Alzheimer's disease. One of the therapeutic agents used in the alleged method of treatment is tacrine hydrochloride (hereinafter referred to as tacrine) which is 9-amino-1,2,3,4-tetrahydroacridine hydrochloride represented by the formula (A):

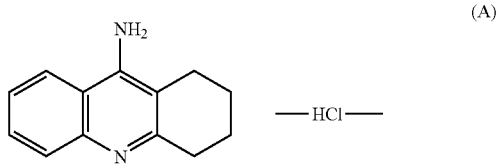

(A)

The mechanism of action of the said agent involves inhibiting choline esterase Volger B. W. "Alternatives in the treatment of memory loss in patient with Alzheimer's disease. (Clinical Pharmacy, 1991 Jun. 10 (6): 447–56). As for the choline esterase inhibiting activity, tacrine is an analogue of the world famous physostigmine and is a traditional anticholine esterase agent. However, the treatment with tacrine is not always effective. Besides, tacrine tends to cause undesirable side-effects.

A wide range of neurological diseases such as Alzheimer's disease. Huntington chores amiotrophic lateral sclerosis as-well as brain ischemia are known to be associated with an excitotoxic effect of neuromediatory excitatory amino acids (EAA) such as glutamate and aspartate (Excitatory Amino Acids and Drug Research, Ed. by M. R. Szewczak N. I. Hrib Alan R. Liss, Inc., New York, 1989, p.380; The NMDA Receptor, Eds. Watkins & Collingridge G., 1989, IRL Press). In accordance with this mechanism, hyperexcitation of neurones in prolonged activation of their N-methyl-D-aspartate (NMDA) receptors with glutamate results in an excessive entry of potassium ions into the cell which initiates a number of pathological metabolic processes finally causing the death of nerve cells (Mattson, Neurone, 1990, v.2, p.105, Mill S. Kater. Neuron, 1990, v.2, p.149; Saitch et al. Lab Suvest. 1991, v.64, p.596).

More specifically in Alzheimer's disease, death of numerous neurones is believed to occur as follows. An endogenic oligopeptide, such as β-amyloid, is a neurotoxic factor inducing neurodegenerative processes in the neurones. β-Amyloid is present in the neurotic plaques abundantly located on the surface of the brain of the patients suffering from Alzheimer's disease (Prelli et al.,—J. Neurochem. 1988, v.51, p. 648; Yanuer et al.,—Science, 1990, v.250, p.279). As shown by the investigations of recent years, β-amyloid significantly enhances the excitotoxic effect of glutamate which is effected through the NMDA-receptor system (Koh et al., Brain Res., 1990, v.533, p.315; Mattson et al.,—J. Neurosci., 1992, v. 12, p.376). As a result, the glutamate mediator at concentrations that are nontoxic under normal conditions becomes toxic for neurones under conditions of the developing β-amyloid dose and causes their death.

In this connection, the search for effective antagonists of the brain NMDA-receptors capable of preventing the realization of the neurotoxic effect of EAA appears to be an original and promising approach to creation of neuroprotectors of a wide spectrum of activity including agents which can prevent the development of Alzheimer's disease and be useful for treatment of such diseases as Alzheimer's disease (Maragos W. F. et al., Trends Neurosci., 1987, No. 10, p.65).

A well known NMDA receptor antagonist is 2-amino-5-phosphonovaleric acid (AP5) (Evans et al.,—Brit. J. Pharmacol., 1982, v.75, p.65). The main disadvantage of AP5 compound a side neurotoxic effect (such as the disturbance of coordination of movement and a sedative effect) which becomes apparent when AP5 is used in the doses in which it produces anti-NMDA effect ($ED_{50}$=190 mg/kg) (Grigoriev et al., Chim. Pharm. Journal, 1988, No.3, p. 275–277). An intensive search for and trials of the agents having the anti-NMDA properties but without the neurotoxic effects is currently under way for treatment to of the neurodegenerative diseases. However, to date such agents have not been available in clinics.

SUMMARY OF THE INVENTION

The present invention provides compounds and methods of using these compounds to treat neurodegenerative diseases, especially Alzheimer's disease.

According to the present invention, the compounds that are provided for the treatment of neurodegenerative diseases can be represented by a general formula (I):

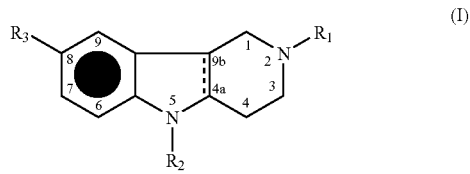

(I)

wherein R₁ is Me, Et or PhCH₂; R₂ is H, PhCH₂ or 6-Me-3-Py-(CH₂)₂; and R₃ is H, Me or Br. The solid line accompanied by the dotted line. i.e.

----- represents a single or double bond and salts thereof with pharmacologically acceptable acids.
When

----- represents a single bond, then R₁=R₃=Me; R₂=H; and the compound is in the form of a cis(±)isomer.
When

----- represents a double bond, then
(i) R₁=Et or PhCH₂, R₂=R₃=H,
(ii) R₁=R₃=Me, R₂=PhCH₂,
(iii) R₁=Me, R₂=6-Me-3-Py-(CH₂)₂, R₃=H,
(iv) R₁=R₃=Me, R₂=6-Me-3-Py-(CH₂)₂,
(v) R₁=Me, R₂=H, R₃=H or Me,
(vi) R₁=Me, R₂=H, R₃=Br.
and salts thereof % with pharmacologically acceptable acids and quaternized derivatives.

Particular examples of the compound described above are:
1. 2-methyl-2,3,4,5-tetrahydro-1H-pyrido[4,3-b]indole;
2. 2,8-dimethyl-2,3,4,5-tetrahydro-1H-pyrido[4,3-b]indole and its methyliodide;
3. cis(±)2,8-dimethyl-2,3,4,4a,5,9b-hexahydro-1H-pyrido[4,3-b]indole and its dihydrochloride;
4. 2-methyl-8-bromo-2,3,4,5-tetrahydro-1H-pyrido[4,3-b]indole and its hydrochloride;
5. 2-ethyl-2,3,4,5-tetrahydro-1H-pyrido[4,3-b]indole;
6. 2-benzyl-2,3,4,5-tetrahydro-1H-pyrido[4,3-b]indole;
7. 2,8-dimethyl-5-benzyl-2,3,4,5-tetrahydro-1H-pyrido[4,3-b]indole and its hydrochloride;
8. 2-methyl-5-[2-(6-methyl-3-pyridyl)ethyl]-2,3,4,5-tetrahydro-1H-pyrido[4,3-b]indole and its sesquisulfate monohydrate:
9. 2,8-dimethyl-5-[2-(6-methyl-3-pyridyl)ethyl]-2,3,4,5-tetrahydro-1H-pyrido[4,3-b]indole and its dihydrochloride.

DETAILED DESCRIPTION OF THE INVENTION

The object of the invention is to provide compounds having a high anti-NMDA activity and producing no side- and toxic effects.

As one of the approaches is to search for such agents in the known chemical compounds, from which the inventors have tried to reveal new unexpected (in this case, anti-NMDA) properties which are not due to the chemical structure of the compounds.

The inventors have carried out large-scale investigations of some known compounds which are tetra- and hexahydro-1H-pyrido[4,3-b]indole derivatives that manifest a broad spectrum of biological activity. In the series of 2,3,4,5-tetrahydro-1H-pyrido[4,3-b]indoles the following types of activity were found: antihistamine activity (OS-DE NN 1.813 229, Dec. 6, 1968; 1.952.80, Oct. 20, 1969), central depressive and antiinflammatory activity (U.S. Pat. No. 3,718,657 Dec. 13, 1970), neuroleptic activity (Herbert C. A., Plattner S. S. Wehch W. N.—Mol. Pharm. 1980, v.17, N 1, p.38–42) and others. 2,3,4,4a,5,9b-hexahydro-1H-pyrido[4,3-b]indole derivatives show psychotropic (Welch W. H., Herbert C. A., Weissman A., Koe K. B. J. Med. Chem. 1986, vol.29, No. 10, p.2093–2099), antiaggressive, antiarrhythmic and other types of activity.

Several drugs such as diazoline (mebhydroline), dimebon, dorastine, carbidine(dicarbine), stobadine, hevotroline based on tetra- and hexahydro-1H-pyrido[4,3-b]indole derivatives are being manufactured. Diazoline(2-methyl-5-benzyl-2,3,4,5-tetrahydro-1H-pyrido[4,3-b]indole dihydrochloride) (Klyuev M. A., Drugs, used in "Medical Pract.", USSR. Moscow, "Meditzina" Publishers, 1991, p.512) and dimebon (2,8-dimethyl-5-(2-(6-methyl-3-pyridyl)ethyl-2,3,4,5-tetrahydro-1H-pyrido[4,3-b]indole dihydrochloride) (M. D. Mashkovsky, "Medicinal Drugs" in 2 vol. Vol. 1—12th Edition. Moscow. "Meditzina" Publishers, 1993, p.383) as well as its closest analogue dorastine(2-methyl-8-chloro-5-[2-(6-methyl-3-pyridyl)ethyl]-2,3,4,5-tetrahydro-1H-pyrido[4,3-b]indole dihydrochloride) (USAN and USP dictionary of drugs names (United States Adopted Names, 1961–1988, current US Pharmacopeia and National Formular for Drugs and other nonproprietary drug names), 1989, 26th Edition., p.196) are known as antihistamine drugs; carbidine (dicarbine) (cis(±)-2,8-dimethyl-2,3,4a,5,9b-hexahydro-1H-pyrido[4,3-b]indole dihydrochloride) is a national neuroleptic agent having an antidepressive effect (L. N. Yakhontov, R. G. Glushkov, Synthetic Drugs, ed. by A. G. Natradze, Moscow, "Meditzina" Publishers, 1983, p.234–237), and its (–)isomer, stobadine, is known as an antiarrythmic agent (Kitlova M., Gibela P., Drimal J., Bratisl. Lek. Listy, 1985, vol.84, No.5, p.542–549); hevotroline (8-fluoro-2)(3-(3-pyridyl)-2,3,4,5-tetrahydro-1H-pyrido[4,3-b]indole dihydrochloride) is an antipsychotic and anxiolytic agent (Abou-Gharbi M., Patel U. R., Webb M. B., Moyer J. A., Ardnee T. H., J. Med. Chem., 1987, vol.30, p.1818–1823).

However no NMDA receptor antagonists have been found so far among tetra- and hexahydro-1H-pyrido[4,3-b]indole derivatives.

The inventors have quite unexpectedly found that hydrogenated pyrido[4,3-b]indole derivatives are endowed with such properties. It has been found in particular, that a number of known hydrogenated pyrido[3,4-b]indole derivatives have NMDA antagonist properties, which makes them useful for treating neurodegenerative diseases, especially Alzheimer's disease.

According to the present invention, the compounds that are provided for the treatment of neurodegenerative diseases can be represented by a general formula (I):

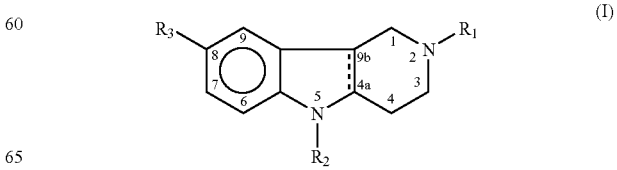

wherein R₁ is Me, Et or PhCH₂; R₂ is H, PhCH₂ or 6-Me-3-Py-(CH₂)₂; and R₃ is H, Me or Br. The solid line accompanied by the dotted line. i.e.

----- represents a single or double bond and salts thereof with pharmacologically acceptable acids.
When

----- represents a single bond, then $R_1=R_2=Me$; $R_2=H$; and the compound is in the form of a cis(±)isomer.
When

----- represents a double bond, then
(i) $R_1=Et$ or $PhCH_2$, $R_2=R_3=H$,
(ii) $R_1=R_3=Me$, $R_2=PhCH_2$,
(iii) $R_1=Me$, $R_2=6-Me-3-Py-(CH_2)_2$, $R_2=H$,
(iv) $R_1=R_2=Me$, $R_2=6-Me-3-Py-(CH_2)_2$,
(v) $R_1=Me$, $R_2=H$, $R_3=H$ or Me,
(vi) $R_1=Me$, $R_2=H$, $R_2=Br$, and salts thereof with pharmacologically acceptable acids and quaternized derivatives.

Particular examples of the compound described above are:
1. 2-methyl-2,3,4,5-tetrahydro-1H-pyrido[4,3-b]indole;
2. 2,8-dimethyl-2,3,4,5-tetrahydro-1H-pyrido[4,3-b]indole and its methyliodide;
3. cis(±)2,8-dimethyl-2,3,4,4a,5,9b-hexahydro-1H-pyrido[4,3-b]indole and its dihydrochloride;
4. 2-methyl-8-bromo-2,3,4,5-tetrahydro-1H-pyrido[4,3-b]indole and its hydrochloride;
5. 2-ethyl-2,3,4,5-tetrahydro-1H-pyrido[4,3-b]indole;
6. 2-benzyl-2,3,4,5-tetrahydro-1H-pyrido[4,3-b]indole;
7. 2,8-dimethyl-5-benzyl-2,3,4,5-tetrahydro-1H-pyrido[4,3-b]indole and its hydrochloride;
8. 2-methyl-5-[2-(6-methyl-3-pyridyl)ethyl]-2,3,4,5-tetrahydro-1H-pyrido[4,3-b]indole and its sesquisulfate monohydrate;
9. 2,8-dimethyl-5-[2-(6-methyl-3-pyridyl)ethyl]-2,3,4,5-tetrahydro-1H-pyrido[4,3-b]indole and its dihydrochloride.

The information of the compounds listed above can be obtained from the publications referred to below.

The synthesis of the compound No. 1 is described by U. Horlein in Chem. Ber., 1954, Bd.87, hft 4, p.463–472. The preparation of the compounds No. 2, 4 and 5 and the information that the properties of serotonine antagonists are disclosed by C. J. Cattanach, A. Cohen and B. H. Brown in J. Chem. Soc. (ser. C) 1968, 1235–1243. The preparation of methyliodide of the compound No. 2 is described by M. A. Yurovskaya and I. L. Rodionov in Khim. Geterots. Soed., 1981, No. 8, p.1072–1078. The data on the preparation and the neuroleptic properties of the compound No 3 can be found in the publication by L. N. Yakhontov and R. G. Glushkova Synthetic Drugs (edited by A. G. Natradze), Moscow, "Meditsina Publishers", 1983, p.234–237. The synthesis of the compound No. 6 is described in the article by N. P. Buu-Hoi, O. Roussel, P. Jacquignon, J. Chem. Soc., 1964, No. 2, p.708–711. The synthesis of the compound No. 7 is described by N. F. Kucherova and N. K. Kochetkov in J. Obshch. Khim., 1956, v. 26, p. 3149–3154, and the preparation of the compounds No. 8 and 9 is reported by A. N. Kost, M. A.-Yurovskaya and T. M. Mrlnikova in "Khim. Geterots. Soed.", 1973, No. 2, p. 207–212.

The fact that the compounds of the formula (I) exhibit anti-NMDA activity is confirmed by the following examples that show the results of the biological experiments that were carried out.

EXAMPLES

1. Anti-NMDA Activity of the Compounds Provided by the Present Invention

The experiment was conducted in white non-inbred male mice of 20–24 g of weight. A solution of the test agent in 0.2 ml of 5% aqueous dimethylsulfoxide was injected intraperitoneally 40 minutes before the injection of NMDA into the lateral vehicle of the brain. For the mice that had been prepared beforehand for the experiment a skin flap on the head of each mouse was removed under ether anesthesia and a hole was bored in the skull by a fine drill. NMDA (0.1 µg) in a volume of 1.4 µl was injected with a microsyringe. The microsyringe needle was immersed to a depth of 2.5 mm. After the operation, the wound was treated with a 2% novocaine solution. After recovery from the anesthesia, the mice showed signs of pain disturbance. The accuracy of NMDA injection was monitored by injection of methylene blue. Two to 4 hours after the operation, the mice were used for a pharmacological experiment.

The animals inoculated with a saline solution were used as control. In the control group the injection of NMDA into the lateral ventricle in a dose of 0.1 µg per mouse caused run, jumps, convulsions and then the death of the animals. In the experimental groups the preinjection of the test substances prevented the development of convulsions and death of the animals.

Each dose of the agent was tested in a croup of 6–8 animals. The $ED_{50}$ value (the dose of the agent preventing the development of convulsions and the death of 50% of the animals) was determined by a probit-analysis method (Litchfild J. T., Wicoxon F. J.—Pharmacol. Exp. Therap., 1949, v. 96, p. 99–114).

The closest prior art agent tacrine characterized above and the known compound AP-5 exhibiting the anti-NMDA activity were tested for comparative purposes.

The test results are summarized in Table A.

It follows from Table A, that the compounds according to the invention have an anti-NMDA activity expressed as $ED_{50}$ in the range of 16–45 mg/kg by intraperitoneal inoculation, i.e. in the pharmacologically acceptable range, and do not show any appreciable neurotoxic effect in the investigated doses.

Thus, the marked NMDA-antagonist properties found in the compounds of formula (I) permit a conclusion on the potential usefulness of the said compounds in the treatment of neurodegenerative diseases, and in particular, Alzheimer's disease.

TABLE A

| No. | $R_1$ | $R_2$ | $R_3$ | Salt | $ED_{50}$(mg/kg, i.p.) |
|---|---|---|---|---|---|
| 1 | Me | H | H | — | 30 ± 4 |
| 2 | Me | H | Me | — | 16 ± 4 |
| 3 | Me | H | Me | MeJ | ~40 |
| 4* | Me | H | Me | 2HCl | 31 ± 7 |
| 5 | Me | H | Br | HCl | 29 ± 5 |
| 6 | Et | H | H | — | 45 ± 6 |
| 7 | PhCH$_2$ | H | H | — | 43 ± 5 |
| 8 | Me | PhCH$_2$ | Me | HCl | 45 ± 5 |
| 9 | ME | 6-Me-3-Py-(CH$_2$)$_2$— | H | 1.5H$_2$SO$_4$.H$_2$O | 22 ± 4 |
| 10** | ME | 6-Me-3-Py-(CH$_2$)$_2$— | Me | 2HCl | 42 ± 6 |
| 11 | Tacrine | | | | not active |
| 12 | AP-5 | | | | 190 ± 20 | i.p.—intraperitoneally
*the "carbidine" agent (hexahydro derivative. cis (±)-isomer: the remaining compounds are tertahydro derivatives)
**the "dimebon" agent II. Clinical Trials of the "Dimebon" Agent The "dimebon" agent (compound No. 10, Table A) which is used in medicine as an antiallergic agent (Inventor's Certificate No. 1138164, IP Class A61K 31/47.5, C07 D 209/52, published on Feb. 7, 1985) was also clinically tested as an agent for treatment of Alzheimer's disease. The carbidine agent (compound No. 4) is less suitable for preliminary clinical tests due to its obvious psychotropic effect capable of masking some manifestations of positive treatment results. Dimebon is non-toxic and does not show any negative side-effects.

The test was carried out under the direct supervision by two of the inventors, namely E. E. Bukatina and V. Grigorieva, in 14 patients who agreed to take part in the tests, 13 of whom lived in a boarding house for senile persons and one patient lived with her family.

The data on the patients (age, sex, place of observation and duration of the disease) is presented in Table 1.

Alzheimer's disease was diagnosed on the basis of criteria ICD-10 NINCDS ADRDA.

The information on the onset and the course of the disease in 7 patients was given by their closest relatives. Six patients (observations 1, 2, 3, 7, 9 and 12) living in the boarding house had no relatives or other persons who could give any information on the time of onset of the first symptoms and the pattern of the course of the disease. However, it is apparent from the medical charts of all the patients that the very first examinations by the doctors revealed distinct disturbances of memory which increased with time. No sharp changes in the condition of the patients during their in the boarding house were found and recorded in the available medical documents and in the doctor's conclusions in the outpatient clinics where the patients had been examined before admission to the boarding house.

From what has been stated above as well as the clinical features of dementia suggested Alzheimer's disease which had started before the admission to the boarding house. In one female (observation 10) progressive decline of memory was noted in the boarding house almost 2 years after her admission.

Dementia of different degree, from the initial to marked manifestations, was found in all cases of the beginning of the investigation. The clinical diagnosis was confirmed by computer tomography (CT) of the brain.

Dimebon in the form of tablets (comprising 10 mg of dimebon, 30 mg of lactose, 5 mg of magnesium stearate was prescribed for oral administration in a dose of 0.02 g three to times a day. The patients living in the boarding house received dimebon for 58 days. A patient (observation 14) who was under outpatient observation continued taking the agent for a month after the completion of the tests.

Before the treatment with dimebon, and at 4 and 8 weeks after treatment the patients were examined according to Hazegawa's scale and the inventors' scale ("Social and Clinical Psychiatry", 1992, No.4, pp.29–37) which includes the following indexes: (1) orientation in locality, time, immediate surroundings and one's own personality; (2) orientation in space; (3) memory for the past; (4) memory for the present; (5) "life in the past"; (6) (a) articulation, (b) difficulty in finding words, and distortion of words; (c) naming of objects; (d) following instructions; (7) concentration (of attention); (8) an affective sphere; (a) high spirits, (b) low spirits; (9) delirium; (10) hearing hallucinations; (11) visual hallucinations; (12) senile or senile-like confusion (when motion anxiety is accompanied by the revival of the past experience); (13) irritability; (14) anxiety; (15) asthenia; (16) headaches; (17) dizziness; (18) tearfulness; (19) spontaneous activity; (20) elementary self-service; and (21 control of sphincters.

According to the Hazegawa's scale, the 0 score indicates the poorest result; on the contrary, according to the inventors' scale, the 0 score indicates the absence of a symptom 4 score indicates the greatest manifestation thereof. At the examination according to the inventors' scale, the decree of disturbance of some function proved to be between the two evaluation indices, the value was of intermediate type, e.g. 0.5, 1.5, or the like. Before the therapy was started, the patients had been independently examined by two doctors who used the inventors' scale. The examination during the treatment was carried out by the doctors using both the scales. The evaluation according to all the inventors' scale points during all the tests and their variations during the treatment with dimebon are given in the Appendix.

According to the inventors' scale, the degree of the disturbance if the cognitive functions was determined by a sum of evaluations according to the first 5 scale points reflecting the condition of memory, orientation and relation with the reality. The disturbance of speech was dealt with separately and was determined by a sum of evaluations according to items 6b-6d. No disturbances of articulation (item 6a) corresponding to peculiar disturbances of speech functions in Alzheimer's disease were observed in any cases.

Both absolute evaluations of the signs under investigation (the evaluation prior to treatment is a mean evaluation of the two examinations) and variations in them were analysed in the course of therapy. In doing so, only those changes that were beyond the range of evaluations obtained in two pre-treatment examinations were taken into consideration.

The test results reflected the condition of the patients at the time of the examination. Any changes in the metal state observed in the interval between the tests and disappearing by the moment of examination according to the scale were described in the section "Clinical Observations".

The statistical data processing was carried out by means of Student's t-test and Fisher's "Fi" criterion.

1. The Examination According to Hazegawa's Scale

The results obtained during the examination of the patients according to Hazegawa's scale are shown in Table 2.

The test results of 7 patients with relatively mild dementia are presented in Table 3. This group included the patients whose evaluation for each of the inventor's 5-point scale did not exceed 2.5 scores. In fact, only one of the patients had such score (observation 2) according to the 3rd scale point (memory for the past). All the other patients had lower scores.

As can be seen from Table 2, against the background of treatment with dimebon there is a trend for improvement which becomes more marked with an increase in the duration of the therapy.

Most close to the significant are the results obtained after 8-week course of treatment of the patients with mild dementia (Table 3): for p<0.05, tst=2.2, td=2.1.

2. The Examination According to the Inventor's Scale

The results according to all the points of the investor's scale are presented in Table 4.

2.1 Cognitive Functions.

The evaluations of the cognitive functions (the sum of evaluations according to the first 5 points of the scale) are presented in Table 5 and their variations in the course of the therapy are shown in Table 6.

As in the case of examinations according to Hazegawa's scale, there was a trend to some improvement in the cognitive functions during the treatment with dimebon, which was more evident when the agent was administered for a longer period (Table 5).

The data of Table 6 clearly shows that after 8 weeks of the therapy there was significantly better improvement in the cognitive functions than after 4 weeks.

Similar Tables (Tables 7 and 8) are provided for the patients who had mild dementia. It follows from these Tables, that in this group of patients there was not only significantly greater improvement in the cognitive functions after the 8-week course of treatment than after the 4-week course (like in the total group of patients), but also significantly different absolute values of the scores before treatment and after 8 weeks of dimebon administration.

The pattern of distribution of the variations according to the first 5 points of the scale reflecting the condition of the cognitive functions (Table 9) reveals the lack of impairments both after 4-week and 8-week treatment. There is also a trend for more improvements with a longer treatment. Slight improvements were significantly more frequent after 8 weeks of the treatment that after 4 weeks.

It may be assumed that the 4-week treatment with dimebon produces positive results at least for the patients suffering from mild dementia. The inventors possess data on AD with a spontaneous course in 8 patients with mild dementia. These patients were observed in the Moscow Boarding House No. 20 in 1988 and given placebo for a month. These patients had received no therapy that could influence cognitive functions in AD.

By the degree of initial dementia (the mean sum of evaluations of two examinations according to the first 5 items of the scale prior to the test), both groups of the patients were comparable: 5.72±0.39 score for the patients in the control group and 6.29±0.7 score for those in the experimental group.

The comparison of the changes of cognitive functions of this and experimental group after 4 weeks showed the following: changes in the cognitive functions in these groups of patients during one month was 0.5±0.14 in the experimental group and 0.12±0.12 in the control group, p<0.01.

2.2 Speech Functions

The evaluation of speech functions (the sum of scores for items bb-6d) during dimebon therapy are presented in Tables 10 and 11.

The data in Table 10 shows some trend for improvement of speech functions during the period of dimebon administration, which was slightly more evident in the prolonged treatment. The distribution pattern of the variations in items 6b-6d reflecting the condition of the speech functions is presented in Table 12.

2.3 Other Scale Values

During the test period none of the patients showed hearing or visual hallucinations (items 10 and 11), senile confusion (item 12) or disturbances of sphincter control (item 21).

As mentioned above, the results of the examinations by all the other items of the scale are presented in Table 4. The mean values in this Table have been calculated for the whole group of the patients examined. The dynamics of those pathological manifestations which according to the data presented in Table 4 have a trend for marked variations during the course of treatment with dimebon are dealt with in more detail below. Only those cases are analysed where the appropriate manifestations occurred prior to or during the treatment.

(a) Depression

Prior to the treatment, 11 patients had various depressive symptoms. At 4 weeks after the treatment with demibon, in 5 patients (45%) the depression abated and there was not a single case of deterioration or emergence of depression. After 8 weeks of treatment, 6 patients showed an improvement (55%). One patient showed signs of aggravation.

The mean values in 12 patients with depressive manifestations prior to the treatment and after 4 and 8 weeks of the treatment were 1.1±0.22, 0.58±0.18 and 0.58±0.14 score, respectively.

The dynamics of depressive manifestations in patients suffering from evident depression prior to the treatment with dimebon (the scores were not less than 1 in both examinations) are presented in Table 13. As can be seen from the Table, abatement of depression was significant after 8 weeks of the treatment. In this case, after the course of the treatment with dimebon, there was a close correlation between the improved cognitive no functions and abated depressive symptoms (Table 14): r=0.8, p<0.01.

The improvement in the values by Hazegawa's scale also correlates with the abatement of depression after 8 weeks of treatment. After 8 weeks r=0.63 and p<0.05, and after 4 weeks r-0.3 and p>0.05.

(b) Delirium

During treatment with dimebon there was not a single case of the first emergence of delirium.

It can be seen from Table 4, that there is a certain trend for abatement of delirious symptoms during the course of treatment. In the analysis of similar relationships among 10 patients who had delirious symptoms prior to the treatment, no obvious differences were found, either. The mean values of delirium manifestations prior to the medical treatment and 4 and 8 weeks after the treatment were 1.28±0.21, 0.8±0.33 and 0.7±0.27, respectively.

(c) Irritability

Not a single observation indicated the aggregation or emergence of irritability during the treatment with dimebon.

Prior to the treatment 7 patients showed irritability (Table 15). As can be seen from the Table, an appreciable reduction in irritability was noted after 8 weeks of the treatment.

(d) Headaches 10 patients complained headaches during the observation period. One of them (observation 14) had the first headaches in the 8th week of the treatment. The other 9 patients had headaches prior to the treatment. The analysis of variations in these symptoms after 4 and 8 weeks of the treatment in comparison with two examinations carried out before the beginning of the treatment showed no aggregation of headaches against the background of the therapy in these cases.

Five patients (50%) showed abatement or complete cessation of headaches after 4 weeks of treatment and 3 patients (30%) showed the same improvement after 8 weeks. The data on the dynamics of the intensity of headaches in the patients who suffered from no them are presented in Table 16. They show that the abatement of headaches was observed 4 weeks after the treatment, and some intensification of these symptoms was observed after 8 weeks.

(e) Tearfulness

Prior to the treatment 5 patients suffered from tearfulness (3 patients showed slight tearfulness). After four weeks 4 female patients showed no sings of it and after 8 weeks not a single female patient suffered from tearfulness.

Prior to the medical treatment and after 4 and 8 weeks of the treatment the mean scores of tearfulness were 0.36±0.18, 0.2±0.18, and 0±0.0, respectively. All the differences are not significant.

3. Clinical Observations

The pattern of the dynamics of the mental states of the patients during the treatment with dimebon registered in clinical observations is presented in Table 17.

Psychopathic-like symptoms (lack of restraint, touchiness, conflict making, evil-mindedness or aggressiveness) in all 7 patients who suffered from them decreased significantly during the first 2 weeks or therapy. A distinct antidepressive effect of the agent was also observed in 8 patients. One of them (observation 10) showed no lower spirits during the test period, but, as the medical stuff reported, she had frequent disphorias which ceased during dimebon administration. Besides, the patient herself (dementia was not profound in this case) constantly emphasized that her mood improved during the treatment.

Only one female patient (observation 14) showed no signs of abatement of depressive manifestations during the test period. This patient continued to take dimebon after the termination of the trial. On the 62nd day of the treatment she noted considerable improvement in her mood which persisted during a month while she was taking the medicinal preparation.

In most other cases normalization of the improvement of the affection occurred soon after the beginning of the therapy: in one patient (observation 7) on the 2nd day, in 2 patients (observations 4 and 10) on the 4th day, in 2 patients (observations 3 and 5) on the 7th or 8th day, in 3 patients (observations 2, 1, 13) on the 11th or 12th day. In two of these patients (observations 1 and 13) the spirits continued to improve and the effect attained after 8 weeks of the treatment was higher than that observed after 4 weeks.

4 patients (observations 1, 2, 7 and, 10) became more active and noted themselves that they experienced a sense of cheerfulness and freshness. 2 patients (observations 4 and 7) slept better, 4 patients (observations 1, 5, 6, and 7) complained of headaches much less frequently during the treatment. 8 patients (observations 1, 2, 3, 4, 7, 8, 10, and 11) displayed a greater interest in what was happening around.

On the whole, the patients became calmer and more sociable, easier to deal with, they began acting and responding more adequately. In some cases (observations 1, 2, 4, 7, and 13) the entire appearance of the patients changed in the estimation of those who were observing them.

4. EEG Investigations

No changes in the EEG during the course of treatment were observed in any patients, except one (observation 12) who had experienced increase of focal $\Delta$-waves and still greater retardation of the rhythm.

Six patients showed the following slight changes in the EEG during the treatment course: a tendency for a greater frequency of the main rhythm (observations 4 and 5), some intensification of the $\beta$-rhythm (observations 5 and 14) (positive dynamics), a great number of acute waves (observations 2 and 5) and paroxysmal symptoms (observation 10), the latter considered to be the negative dynamics. In observations 2, 11 and 14 the weakly positive dynamics of the EEG was manifested in weaker outbursts during hyperventilation and normalization of the zonal differences.

5. Blood and Urea Analysis

No pathologic changes in the hematological and biochemical statutes were found during the course of the treatment. There was a significant reduction in the amount of leukocytes (within normal limits) after 4 weeks of the treatment, $p<0.05$. By the 8th week of the treatment the amount of leukocytes was normal again.

6. Conclusion

A pilot research of the effectiveness of dimebon in 14 patients suffering from Alzheimer's disease revealed definite positive effect of the agent on psychopatic-like and depressive manifestations. The examinations carried out using Hazegawa's scale and the inventor's scale revealed a significant improvement in cognitive functions especially in patients with mild dementia.

The results obtained in the studies attest the therapeutic activity of dimebon in the treatment of Alzheimer's disease.

TABLE 1

Distribution of Patients According to Age, Sex. Observation Place and Duration of the Disease

| No | Age | Sex | Observation place | Residence time in boarding house | Duration of the disease |
| --- | --- | --- | --- | --- | --- |
| 1 | 87 | f | boarding house | 2 years and 3 months | more than 2 years and 3 months |
| 2 | 83 | f | boarding house | 6 months | more than 6 months |
| 3 | 74 | m | boarding house | 1 year and 4 months | more than 1 year and 4 months |
| 4 | 87 | f | boarding house | 1 year and 5 months | 7 years |
| 5 | 87 | f | boarding house | 2 years and 11 months | 3 years |
| 6 | 88 | f | boarding house | 1 year and 9 months | 5 years |
| 7 | 85 | f | boarding house | 1 year and 4 months | more than 1 year and 4 months |
| 8 | 83 | f | boarding house | 1 year and 4 months | 4 years |
| 9 | 83 | f | boarding house | 1 year and 5 months | more that 1 year and 5 months |
| 10 | 85 | f | boarding house | 3 years and 8 months | 2 years |
| 11 | 81 | f | boarding house | 1 year | 1 year and a half |
| 12 | 81 | f | boarding house | 1 year and 11 months | more than 1 year and 11 months |
| 13 | 80 | f | boarding house | 2 years | 9 years |
| 14 | 64 | f | out-patients clinic | — | 9 years |

TABLE 2

Evaluation according to Hazegawa's Scale Prior to and after 4 and 8 Weeks of Treatment with Dimebon

| Nos | Prior to med. treatment | After 4 weeks | After 8 weeks |
|---|---|---|---|
| 1 | 14 | 22 | 19 |
| 2 | 14 | 13.5 | 20 |
| 3 | 24.5 | 24 | 28.5 |
| 4 | 19 | 26.5 | 25.5 |
| 5 | 2.5 | 2.5 | 4.5 |
| 6 | 12.5 | 13.5 | 15 |
| 7 | 2 | 7.5 | 2 |
| 8 | 11.5 | 14.5 | 23.5 |
| 9 | 15.5 | 14.5 | 9 |
| 10 | 25.5 | 19 | 25.5 |
| 11 | 7 | 13 | 9.5 |

TABLE 2-continued

Evaluation according to Hazegawa's Scale Prior to and after 4 and 8 Weeks of Treatment with Dimebon

| Nos | Prior to med. treatment | After 4 weeks | After 8 weeks |
|---|---|---|---|
| 12 | 3.5 | 2 | 4.5q |
| 13 | 7 | 7 | 7 |
| 14 | 24.5 | 26 | 25 |
| M +/− m | 12.35 +/− 1.95 | 14.68 +/− 1.87 | 15.68 +/− 2.39 |
| P | | insignificant | insignificant |

TABLE 3

Evaluation according to Hazegawa's Scale Prior to and after 4 and 8 Weeks of Treatment with Dimebon in Patients with Nonprofound Dementia

| Nos | Prior to med. treatment | After 4 weeks | After 8 weeks |
|---|---|---|---|
| 1 | 14 | 22 | 19 |
| 2 | 14 | 13.5 | 20 |
| 3 | 24.5 | 24 | 28.5 |
| 4 | 19 | 26.5 | 25.5 |
| 8 | 11.5 | 14.5 | 23.5 |
| 10 | 25.5 | 19 | 25.5 |
| 14 | 24.5 | 26 | 25 |
| M +/− m | 19 +/− 2.04 | 20.79 +/− 1.85 | 23 +/− 1.17 |
| P | | insignificant | $t_d = 2.1$ $p \approx 0.05$ $t_{st} = 2.2$ |

TABLE 4

Mean Values according to All Points of the Inventor's Scale prior to and after 4 and 8 Weeks of the Demibon Treatment and Their Variations during the Treatment in Relation to Two Examinations prior to the Treatment

| | Mean values, scores | | | Changes during the course of the therapy, scores | |
|---|---|---|---|---|---|
| No | prior to med. treatment | after 4 weeks | after 8 weeks | after 4 weeks | after 8 weeks |
| 1 | 1.82 +/− 0.19 | 1.75 +/− 0.23 | 1.57 +/− 0.23 | +0.11 +/− 0.07 | +0.18 +/− 0.08 |
| 2 | 0.54 +/− 0.16 | 0.32 +/− 0.15 | 0.25 +/− 0.13 | +0.11 +/− 0.07 | +0.11 +/− 0.07 |
| 3 | 2.34 +/− 0.23 | 2.29 +/− 0.21 | 1.93 +/− 0.24 | +0.07 +/− 0.07 | +0.29 +/− 0.1 |
| 4 | 2.38 +/− 0.22 | 2.21 +/− 0.22 | 1.86 +/− 0.23 | 0 +/− 0 | −0.29 +/− 0.08 |
| 5 | 1.86 +/− 0.21 | 1.75 +/− 0.27 | 1.57 +/− 0.27 | +0.14 +/− 0.08 | −0.29 +/− 0.1 |
| 6b | 0.57 +/− 0.18 | 0.43 +/− 0.17 | 0.39 +/− 0.2 | 0 +/− 0 | −0.04 +/− 0.03 |
| 6a | 0.89 +/− 0.23 | 0.71 +/− 0.21 | 0.54 +/− 0.21 | +0.11 +/− 0.07 | +0.14 +/− 0.08 |
| 6g | 0.64 +/− 0.17 | 0.46 +/− 0.16 | 0.54 +/− 0.19 | −0.07 +/− 0.12 | −0.07 +/− 0.18 |
| 7 | 1.9 +/− 0.27 | 1.75 +/− 0.26 | 1.75 +/− 0.3 | 0 +/− 0.5 | −0.04 +/− 0.06 |
| 8b | 0.95 +/− 0.22 | 0.5 +/− 0.16 | 0.46 +/− 0.14 | +0.41 +/− 0.17 | +0.43 +/− 0.2 |
| 9 | 0.91 +/− 0.2 | 0.57 +/− 0.29 | 0.5 +/− 0.19 | +0.07 +/− 0.09 | +0.25 +/− 0.17 |
| 13 | 0.57 +/− 0.19 | 0.21 +/− 0.15 | 0.14 +/− 0.09 | +0.29 +/− 0.13 | +0.36 +/− 0.16 |
| 14 | 0.38 +/− 0.09 | 0.29 +/− 0.12 | 0.18 +/− 0.1 | −0.04 +/− 0.13 | +0.07 +/− 0.09 |
| 15 | 0.13 +/− 0.06 | 0.18 +/− 0.1 | 0.04 +/− 0.03 | −0.11 +/− 0.09 | 0 +/− 0 |
| 16 | 1.02 +/− 0.27 | 0.32 +/− 0.21 | 0.64 +/− 0.24 | +0.54 +/− 0.21 | +0.21 +/− 0.1 |
| 17 | 0.64 +/− 0.19 | 0.71 +/− 0.27 | 0.68 +/− 0.25 | −0.14 +/− 0.17 | −0.18 +/− 0.22 |
| 18 | 0.36 +/− 0.18 | 0.07 +/− 0.07 | 0.14 +/− 0.14 | −0.14 +/− 0.14 | +0.21 +/− 0.15 |
| 19 | 1.36 +/− 0.22 | 1.29 +/− 0.22 | 1.18 +/− 0.27 | 0 +/− 0 | +0.04 +/− 0.11 |
| 20 | 0.13 +/− 0.08 | 0.07 +/− 0.07 | 0.14 +/− 0.4 | +0.07 +/− 0.07 | 0 +/− 0.1 |

Notes to the Table

As can be seen from items 6a, 10, 11, 12, and 21, no disorders were found in any case.
Here and hereinafter "+" denotes improvement, "−" denotes deterioration of function.
No significant differences were found in any of the scale points.

TABLE 5

Values of Cognitive Function (Sum of Values according to First 5 Scale Points) Prior to and after 4 and 8 Weeks of Treatment with Demibon

| Nos | Mean values of 2 examinations prior to the treatment | After 4 weeks | After 8 weeks |
|---|---|---|---|
| 1 | 8 | 5.5 | 3 |
| 2 | 8.5 | 8.5 | 5 |
| 3 | 4.25 | 3.5 | 2 |
| 4 | 7.5 | 6.5 | 5 |
| 5 | 12.5 | 12 | 12 |

TABLE 5-continued

Values of Cognitive Function (Sum of Values according to First 5 Scale Points) Prior to and after 4 and 8 Weeks of Treatment with Demibon

| Nos | Mean values of 2 examinations prior to the treatment | After 4 weeks | After 8 weeks |
|---|---|---|---|
| 6 | 8.5 | 9.5 | 7 |
| 7 | 13.25 | 10 | 12 |
| 8 | 7.5 | 8 | 6 |
| 9 | 12 | 12 | 11.5 |
| 10 | 4.25 | 3 | 3 |
| 11 | 9 | 8.5 | 8 |
| 12 | 15 | 15 | 13 |
| 13 | 12 | 11 | 10.5 |
| 14 | 4 | 3.5 | 3 |
| M +/- m | 9.02 +/- 0.9 | 8.32 +/- 0.93 | 7.21 +/- 0.82 |
| P | | insignificant | insignificant |

TABLE 6

Variations of Cognitive Function with Respect to Two Examinations Prior to and after 4 and 8 Weeks of Treatment with Demibon

| Observation Nos | Duration of the treatment | |
|---|---|---|
| | 4 weeks | 8 weeks |
| 1 | +1 | +3 |
| 2 | 0 | +2 |
| 3 | +0.5 | +2 |
| 4 | +0.5 | +3 |
| 5 | +0.5 | +0.5 |
| 6 | 0 | +1.5 |
| 7 | +2 | +1 |
| 8 | 0 | +0.5 |
| 9 | 0 | 0 |
| 10 | +1 | +1 |
| 11 | 0 | 0 |
| 12 | 0 | +0.5 |
| 13 | 0 | 0 |
| 14 | +0.5 | +1 |

TABLE 6-continued

Variations of Cognitive Function with Respect to Two Examinations Prior to and after 4 and 8 Weeks of Treatment with Demibon

| Observation Nos | Duration of the treatment | |
|---|---|---|
| | 4 weeks | 8 weeks |
| M +/- m | -0.43 +/- 0.15 | +1.14 +/- 0.26 |
| P | <0.05 | |

TABLE 7

Values of Cognitive Functions Prior to and after 4 and 8 Weeks of Treatment with Demibon in Patients with Unprofound Dementia

| Nos | Mean values of 2 examinations prior to the treatment | After 4 weeks | After 8 weeks |
|---|---|---|---|
| 1 | 8 | 5.5 | 3 |
| 2 | 8.5 | 8.5 | 5 |
| 3 | 4.25 | 3.5 | 2 |
| 4 | 7.5 | 6.5 | 5 |
| 8 | 7.5 | 8 | 6 |
| 10 | 4.25 | 3 | 3 |
| 14 | 4 | 3.5 | 3 |
| M +/- m | 6.29 +/- 0.795 | 5.5 +/- 0.79 | 3.93 +/- 0.5 |
| P | | insignificant | <0.05 |

TABLE 8

Variations of Cognitive Function with Respect to Two Examinations Prior to and after 4 and 8 Weeks of Treatment with Demibon in Patients with Unprofound Dementia

| Observation Nos | Duration of the treatment | |
|---|---|---|
| | 4 weeks | 8 weeks |
| 1 | +1 | +3 |
| 2 | 0 | +2 |
| 3 | +0.5 | +2 |
| 4 | +0.5 | +3 |
| 8 | 0 | +0.5 |
| 10 | +1 | +1 |
| 14 | +0.5 | +1 |
| M +/- m | +0.5 +/- 0.14 | +1.79 +/- 0.35 |
| P | <0.05 | |

TABLE 9

Distribution of Veriations accoding to First 5 Scale Points which Indicate the State of Cognitive Functions during 4 and 8 Weeks of Treatment with Demibon

| Duration of the treatment | | 4 weeks | | | | 8 weeks | | | |
|---|---|---|---|---|---|---|---|---|---|
| Variations | | slight | moderate | marked | total | slight | moderate | marked | total |
| Improve- | abs. | 4* | 4 | — | 8 | 18* | 6 | — | 24 |
| ments | % | 5.7* | 5.7 | — | 11.4 | 25.7* | 8.6 | — | 34.3 |
| Deterio- | abs. | — | — | — | — | — | — | — | — |

TABLE 9-continued

Distribution of Veriations accoding to First 5 Scale Points which Indicate the State of Cognitive Functions during 4 and 8 Weeks of Treatment with Demibon

| Duration of the treatment | | 4 weeks | | | | 8 weeks | | | |
|---|---|---|---|---|---|---|---|---|---|
| Variations | | slight | moderate | marked | total | slight | moderate | marked | total |
| rations | % | — | — | — | — | — | — | — | — |
| No variations | abs. | | 57 | | | | 41 | | |
| | % | | 81.4 | | | | 53.6 | | |
| X | abs. | | 5 | | | | 5 | | |
| | % | | 7.1 | | | | 7.1 | | |

Notes to the Table:
Slight variations by 0.5 score
Moderarte variations by 1 score
Marked variations by more than 1 score
X - No variations in the function prior to and during the treatment
*$p < 0.05$

TABLE 10

Evaluation of Speech Function (Sum of Values according to Items 6b–bd) in scores prior to and after 4 and 8 Weeks of Treatment with Demibon

| Nos | Mean values of 2 examinations prior to the treatment | After 4 weeks | After 8 weeks |
|---|---|---|---|
| 1 | 0.25 | 0 | 0 |
| 2 | 1.5 | 0 | 0 |
| 3 | 0 | 0 | 0 |
| 4 | 1 | 0 | 0 |
| 5 | 4 | 3 | 2 |
| 6 | 2 | 1 | 1 |
| 7 | 5 | 4.5 | 6 |
| 8 | 0.5 | 1 | 0 |
| 9 | 0.75 | 1.5 | 1 |
| 10 | 0 | 0 | 1 |
| 11 | 2 | 1.5 | 0 |
| 12 | 6.25 | 5 | 4.5 |
| 13 | 3 | 2 | 1 |
| 14 | 3.25 | 3 | 3 |
| M +/− m | 2.11 +/− 0.5 | 1.61 +/− 0.44 | 1.39 +/− 0.47 |
| P | | insignificant | insignificant |

TABLE 11

Variations of Speech Function with Respect to Two Examinations Prior to and after 4 and 8 Weeks of Treatment with Demibon

| Observation | Duration of the treatment | |
|---|---|---|
| Nos | 4 weeks | 8 weeks |
| 1 | 0 | 0 |
| 2 | 0 | 0 |
| 3 | 0 | 0 |
| 4 | +1 | +1 |
| 5 | +0.5 | +0.5 |
| 6 | 0 | 0 |
| 7 | 0 | −1.5 |
| 8 | −1 | 0 |
| 9 | 0 | −1 |
| 10 | 0 | −1 |
| 11 | 0 | +1.5 |
| 12 | +1 | +0.5 |
| 13 | +1 | +1 |
| 14 | 0 | −0.5 |
| M +/− m | −0.18 +/− 0.14 | −0.04 +/− 0.22 |
| P | | insignificant |

TABLE 12

Distribution of Venations accoding to Items 6b. c. d of the Scale Points which Indicate the State of Speech Functions during 4 and 8 Weeks of Treatment with Demibon

| Duration of the treatment | | 4 weeks | | | | 8 weeks | | | |
|---|---|---|---|---|---|---|---|---|---|
| Variations | | slight | moderate | marked | total | slight | moderate | marked | total |
| Improvements | abs. | 1 | 3 | — | 4 | 3 | 3 | — | 6 |
| | % | 2.4 | 7.14 | — | 9.5 | 7.14 | 7.1 | — | 14.3 |
| Deteriorations | abs. | — | 1 | — | 1 | 1 | 2 | 1 | 4 |
| | % | — | 2.4 | — | 2.4 | 2.4 | 4.8 | 2.4 | 9.6 |

TABLE 12-continued

Distribution of Venations accoding to Items 6b. c. d of
the Scale Points which Indicate the State of Speech Functions
during 4 and 8 Weeks of Treatment with Demibon

| Duration of the treatment | | 4 weeks | | | | 8 weeks | | |
|---|---|---|---|---|---|---|---|---|
| Variations | | slight | moderate | marked | total | slight | moderate | marked | total |
| No vari- | abs. | | 23 | | | | 19 | | |
| ations | % | | 54.8 | | | | 45.2 | | |
| X | abs. | | 14 | | | | 13 | | |
| | % | | 33.3 | | | | 30.95 | | |

Notes to the Table:
Slight variations by 0.5 score
Moderarte variations by 1 score
Marked variations by more than 1 score
X - No variations in the function prior to and during the treatment

TABLE 13

The Dynamics of Marked Depressive Manifestation in Patients Having
Depression Value of at least 1 Score for Two Examinations prior
to and after 4 and 8 Weeks of Treatment with Dimebon

| | Values. scores | | |
|---|---|---|---|
| Nos | Prior to treatment | After 4 weeks | After 8 weeks |
| 1 | 1.75 | 1 | 0.5 |
| 2 | 1.5 | 0 | 0.5 |
| 3 | 1 | 0.5 | 0 |
| 4 | 3 | 1 | 1 |
| 5 | 1 | 0 | 0 |
| 9 | 0 | 0 | 1 |
| 11 | 1 | 1 | 1 |
| 14 | 1.75 | 3 | 1.5 |
| M +/- m | 1.38 +/- 0.29 | 0.69 +/- 0.23 | 0.69 +/- 0.18 |
| P | insignificant | | <0.05 |

TABLE 14

Correlation between Variations in Cognitive Functions
and Variations in Depressive Manifestations after
4 and 8 Weeks of Treatment with Demibon

| | after 4 weeks | | after 8 weeks | |
|---|---|---|---|---|
| Nos | Variations in cognitive functions | Variations in depressive functions | Variations in cognitive functions | Variations in depressive functions |
| 1 | +1 | +0.5 | +3 | +1.5 |
| 2 | 0 | +1.5 | +2 | +1 |
| 3 | +0.5 | +0.5 | +2 | +1 |
| 4 | +0.5 | +2 | +3 | +2 |
| 5 | +0.5 | +1 | +0.5 | +1 |
| 6 | 0 | 0 | +1.5 | 0 |
| 7 | +2 | 0 | +1 | 0 |
| 8 | 0 | 0 | +0.5 | 0 |
| 9 | 0 | 0 | 0 | -1 |
| 10 | +1 | 0 | +1 | 0 |
| 11 | 0 | 0 | 0 | 0 |
| 12 | 0 | 0 | +0.5 | +0.5 |
| 13 | 0 | 0 | 0 | 0 |
| 14 | -0.5 | 0 | -1 | 0 |
| n | -0.02 | | 0.8 | |
| P | insignificant | | <0.01 | |

TABLE 15

Evaluation of the Degree of Irritability in Scores prior
to and after 4 and 8 Weeks of Treatment with Dimebon
Having these Symptoms in the Clinical Picture

| | Values. scores | | |
|---|---|---|---|
| Nos | Prior to treatment | After 4 weeks | After 8 weeks |
| 2 | 0.5 | 0 | 0 |
| 3 | 1.5 | 0 | 0 |
| 4 | 1 | 0 | 0 |
| 5 | 1.75 | 2 | 0 |
| 7 | 0.5 | 0 | 0 |
| 10 | 0.75 | 0 | 1 |
| 13 | 2 | 1 | 1 |
| M +/- m | 1.14 +/- 0.21 | 0.43 +/- 0.28 | 0.29 +/- 5.17 |
| P | insignificant | | <0.01 |

TABLE 16

Evaluation of Intensity of Headache in Scores prior
to and after 4 and 8 Weeks of Treatment with Dimebon
Having these Symptoms in the Clinical Picture

| | Values. scores | | |
|---|---|---|---|
| Nos | Prior to treatment | After 4 weeks | After 8 weeks |
| 1 | 0.5 | 0.5 | 0 |
| 2 | 1 | 0 | 1 |
| 4 | 2 | 1 | 2 |

TABLE 16-continued

Evaluation of Intensity of Headache in Scores prior to and after 4 and 8 Weeks of Treatment with Dimebon Having these Symptoms in the Clinical Picture

| Nos | Prior to treatment | After 4 weeks | After 8 weeks |
|---|---|---|---|
| 5 | 2.25 | 0 | 1.5 |
| 6 | 0.25 | 0 | 0.5 |
| 7 | 2.5 | 0 | 0 |
| 10 | 2.25 | 0 | 0 |
| 11 | 2.5 | 3 | 3 |
| 12 | 1 | 0 | 0 |
| 14 | 0 | 0 | 1 |
| M +/− m | 1.43 +/− 0.29 | 0.45 +/− 0.29 | 0.9 +/− 0.31 |
| P | | <0.05 | insignificant |

Notes to the Table:
Psychopatic-like manifestations: lack of restraint. touchiness. conflict making, evil-mindedness. aggressiveness. During the test period one female patient (observation 10) did not show low spirits. but prior to the treatment she had frequent disphorias.

TABLE 17

Test Results according to E. E. Bukatina et al. Scale

| Patient No. | K1 | K2 | 4 weeks | Changes | 8 weeks | Changes |
|---|---|---|---|---|---|---|
| *1. Orientation in locality and time* | | | | | | |
| 1 | 1.5 | 1.5 | 1.5 | — | 1 | +0.5 |
| 2 | 1.5 | 2 | 2 | — | 1.5 | — |
| 3 | 1 | 1 | 1 | — | 0.5 | +0.5 |
| 4 | 1.5 | 2 | 1 | +0.5 | 1 | +0.5 |
| 5 | 2 | 3 | 2.5 | — | 2 | — |
| 6 | 2 | 1.5 | 2 | — | 2 | — |
| 7 | 3.5 | 2 | 2 | — | 3 | — |
| 8 | 1.5 | 2 | 2 | — | 1.5 | — |
| 9 | 2 | 2 | 2 | — | 2 | — |
| 10 | 1 | 1 | 0 | +1 | 0 | +1 |
| 11 | 2 | 1.5 | 2 | — | 2 | — |
| 12 | 3 | 3.5 | 3.5 | — | 3 | — |
| 14 | 0.5 | 0.5 | 0.5 | — | 0.5 | — |
| *2. Orientation in space* | | | | | | |
| 1 | 1 | 2 | 0 | —1 | 0 | +1 |
| 2 | 0.5 | 0 | 0 | — | 0 | — |
| 3 | 0 | 0 | 0 | — | 0 | — |
| 4 | 0 | 0 | 0 | — | 0 | — |
| 5 | 1.5 | 1.5 | 1 | −0.5 | −1 | +0.5 |
| 6 | 0 | 0 | 0 | — | 0 | — |
| 7 | 1 | 0 | 0 | — | 0 | — |
| 8 | 0 | 0.5 | 0 | — | 0 | — |
| 9 | 1.5 | 1.5 | 1.5 | — | 1.5 | — |
| 10 | 0 | 0 | 0 | — | 0 | — |
| 11 | 0.5 | 0 | 0.5 | — | 0 | — |
| 12 | 1 | 1.5 | 1.5 | — | 1 | — |
| 13 | 1 | 0 | 0 | — | 0 | — |
| 14 | 0 | 0 | 0 | — | 0 | — |
| *4. Memory for the present* | | | | | | |
| 1 | 2.5 | 1.5 | 1.5 | — | 1 | −0.5 |
| 2 | 2.5 | 2 | 2 | — | 1 | +1 |
| 3 | 1 | 1 | 1 | — | 0.5 | +0.5 |
| 4 | 2 | 2.5 | 2 | — | 1.5 | +0.5 |
| 5 | 3 | 3.5 | 3 | — | 3 | — |
| 6 | 3 | 2.5 | 3 | — | 2 | +0.5 |
| 7 | 3.5 | 2.5 | 3 | — | 3 | — |
| 8 | 2 | 2 | 2 | — | 1.5 | −0.5 |
| 9 | 2.5 | 3 | 3 | — | 2.5 | — |
| 10 | 1.5 | 1 | 1 | — | 1 | — |
| 11 | 3 | 2 | 2 | — | 2 | — |
| 12 | 3.5 | 4 | 3.5 | — | 3 | +0.5 |
| 13 | 4 | 3 | 3 | — | 3 | — |
| 14 | 1 | 1 | 1 | — | 1 | — |
| *5. Life in the past* | | | | | | |
| 1 | 1.5 | 1 | 1 | — | 0.5 | +0.5 |
| 2 | 1.5 | 2 | 1.5 | — | 1 | +0.5 |
| 3 | 1 | 1.5 | 0.5 | +0.5 | 0.5 | +0.5 |
| 4 | 1.5 | 1.5 | 1.5 | — | 0.5 | +1 |
| 5 | 2 | 3 | 2.5 | — | 3 | — |
| 6 | 2 | 2 | 2 | — | 1 | +1 |
| 7 | 3 | 3 | 2 | +1 | 3 | — |
| 8 | 1.5 | 2 | 2 | — | 1.5 | — |
| 9 | 3 | 2.5 | 2.5 | — | 2.5 | — |
| 10 | 0.5 | 1 | 1 | — | 0.5 | — |
| 11 | 2 | 2 | 2 | — | 2 | — |
| 12 | 3 | 3 | 3 | — | 3 | — |
| 13 | 3 | 2 | 2.5 | — | 2.5 | — |
| 14 | 1 | 1 | 0.5 | +0.5 | 0.5 | +0.5 |
| *6b. Difficulty in finding words* | | | | | | |
| 1 | 0.5 | 0 | 0 | — | 0 | 0 |
| 2 | 1 | 0 | 0 | — | 0 | — |
| 3 | 0 | 0 | 0 | — | 0 | — |
| 4 | 0 | 0 | 0 | — | 0 | — |
| 5 | 0 | 1.5 | 1 | — | 0 | — |
| 6 | 0.5 | 0 | 0 | — | 0 | — |
| 7 | 2.5 | 1 | 1.5 | — | 1.5 | — |
| 8 | 0 | 0 | 0 | — | 0 | — |
| 9 | 0 | 0.5 | 0.5 | — | 0 | — |
| 10 | 0 | 0 | 0 | — | 0 | — |
| 11 | 0.5 | 0 | 0 | — | 0 | — |
| 12 | 2 | 2.5 | 2 | — | 2 | — |
| 13 | 1 | 0 | 0 | — | 0 | — |
| 14 | 1 | 1.5 | 1 | — | 2 | −0.5 |
| *6c. Naming of objects* | | | | | | |
| 1 | 0 | 0 | 0 | — | 0 | — |
| 2 | 0 | 0 | 0 | — | 0 | — |
| 3 | 0 | 0 | 0 | — | 0 | — |
| 4 | 0 | 0 | 0 | — | 0 | — |
| 5 | 1.5 | 2 | 1 | +0.5 | 1 | +0.5 |
| 6 | 0 | 1.5 | 0 | — | 0 | — |
| 7 | 3 | 2 | 2 | — | 2 | — |
| 8 | 1 | 0 | 0 | — | 0 | — |
| 9 | 0 | 1 | 1 | — | 0 | — |
| 10 | 0 | 0 | 0 | — | 0 | — |
| 11 | 1 | 1 | 1 | — | 0 | +1 |
| 12 | 2 | 2 | 1 | −1 | 1.5 | +0.5 |
| 13 | 2 | 1 | 2 | — | 1 | — |
| 14 | 2 | 2 | 2 | — | 2 | +0.5 |
| *6d. Performing instructions* | | | | | | |
| 1 | 0 | 0 | 0 | — | 0 | — |
| 2 | 0 | 2 | 0 | — | 0 | — |
| 3 | 0 | 0 | 0 | — | 0 | — |
| 4 | 1 | 1 | 0 | +1 | 0 | +1 |
| 5 | 1 | 2 | 1 | — | 1 | — |
| 6 | 1 | 1 | 1 | — | 1 | — |
| 7 | 1 | 0.5 | 1 | — | 2.5 | −1.5 |
| 8 | 0 | 0 | 1 | −1 | 0 | — |
| 9 | 0 | 0 | 0 | — | 1 | −1 |
| 10 | 0 | 0 | 0 | — | 1 | −1 |
| 11 | 1 | 0.5 | 0.5 | — | 0 | +0.5 |
| 12 | 1 | 3 | 2 | — | 1 | — |
| 13 | 1 | 1 | 0 | +1 | 0 | +1 |
| 14 | 0 | 0 | 0 | — | 0 | 0 |
| *7. Concentration* | | | | | | |
| 1 | 1 | 2 | 1.5 | — | 1 | — |
| 2 | 2 | 1 | 1.5 | — | 1 | — |
| 3 | 0.5 | 0 | 0 | — | 0 | — |
| 4 | 2 | 0.5 | 1 | — | 1 | — |
| 5 | * | 3 | 3 | — | 3 | — |
| 6 | 1.5 | 2 | 2 | — | 2 | — |
| 7 | 3.5 | 4 | 3 | +0.5 | 3.5 | — |
| 8 | 1 | 1.5 | 2 | −0.5 | 2 | −0.5 |
| 9 | 1 | 1.5 | 1 | — | 1 | — |

TABLE 17-continued

Test Results according to E. E. Bukatina et al. Scale

| Patient No. | K1 | K2 | 4 weeks | Changes | 8 weeks | Changes |
|---|---|---|---|---|---|---|
| 10 | 1 | 1.5 | 1 | — | 1 | — |
| 11 | 3 | 3 | 3 | — | 2.5 | +0.5 |
| 12 | 3 | 3.5 | 3 | — | 4 | −0.5 |
| 13 | 1.5 | 3 | 2 | — | 2 | — |
| 14 | 0.5 | 0.5 | 0.5 | — | 0.5 | — |
| 8b. Lower spirits | | | | | | |
| 1 | 1.5 | 2 | 1 | +0.5 | 0.5 | +1.5 |
| 2 | 1.5 | 1.5 | 0 | +0.5 | 0.5 | +1 |
| 3 | 1 | 1 | 0.5 | +0.5 | 0 | +1 |
| 4 | 3 | 3 | 1 | +2 | 1 | +2 |
| 5 | 1 | 1 | 0 | +1 | 0 | +1 |
| 6 | 0 | 1 | 0 | — | 0 | — |
| 7 | 0 | 1 | 0 | — | 0 | — |
| 8 | 0 | 0 | 0 | — | 0 | — |
| 9 | 0 | 0 | 0 | — | 1 | −1 |
| 10 | 0 | 0 | 0 | — | 0 | — |
| 11 | 1 | 1 | 1 | — | 1 | — |
| 12 | 1 | 0.5 | 0.5 | — | 0 | +0.5 |
| 13 | 1 | 0 | 1 | — | 1 | — |
| 14 | 2 | 1.5 | 2 | — | 1.5 | −5 |
| 9. Delirium | | | | | | |
| 1 | 0 | 0 | 0 | — | 0 | — |
| 2 | 0 | 0 | 0 | — | 0 | — |
| 3 | 0 | 0 | 0 | — | 0 | — |
| 4 | 2 | 1.5 | 1 | +0.5 | 0 | +1.5 |
| 5 | 1 | 1.5 | 0 | +1 | 1.5 | 0 |
| 6 | 1 | 0 | 0 | — | 0 | 0 |
| 7 | 2.5 | 1 | 1 | — | 1 | — |
| 8 | 2 | 2 | 2.5 | −0.5 | 2 | — |
| 9 | 1 | 2 | 1.5 | — | 1.5 | — |
| 10 | 0 | 1 | 0 | — | 1 | — |
| 11 | 1 | 0 | 0 | — | 0 | — |
| 12 | 2 | 0 | 0 | — | 0 | — |
| 13 | 2 | 2 | 2 | — | 0 | +2 |
| 14 | 0 | 0 | 0 | — | 0 | — |
| 13. Irritability | | | | | | |
| 1 | 0 | 0 | 0 | — | 0 | — |
| 2 | 0 | 0.5 | 0 | — | 0 | — |
| 3 | 1.5 | 1.5 | 0 | +1.5 | 0 | +1.5 |
| 4 | 1 | 1 | 0 | +1 | 0 | +1 |
| 5 | 2 | 1.5 | 2 | — | 0 | −1.5 |
| 6 | 0 | 0 | 0 | — | 0 | — |
| 7 | 0 | 1 | 0 | — | 0 | — |
| 8 | 0 | 0 | 0 | — | 0 | — |
| 9 | 0 | 0 | 0 | — | 0 | — |
| 10 | 1 | 0.5 | 0 | +0.5 | +1 | — |
| 11 | 0 | 0 | 0 | — | 0 | — |
| 12 | 0 | 0 | 0 | — | 0 | — |
| 13 | 2 | 2 | 1 | +1 | 1 | +1 |
| 14 | 0 | 0 | 0 | — | 0 | 0 |
| 14. Anxiety | | | | | | |
| 1 | 0.5 | 0 | 0 | — | 0 | — |
| 2 | 1 | 0 | 0 | — | 0 | — |
| 3 | 1 | 0.5 | 0 | +0.5 | 0 | +0.5 |
| 4 | 1 | 1 | 0 | +1 | 0 | +1 |
| 5 | 0 | 1 | 1 | — | 0 | — |
| 6 | 0.5 | 0 | 0 | — | 0 | — |
| 7 | 0 | 0 | 0 | — | 0 | — |
| 8 | 0 | 1 | 1 | — | 1 | — |
| 9 | 0 | 0 | 1 | −1 | 0 | — |
| 10 | 0 | 1.5 | 0 | — | 1 | — |
| 11 | 0 | 0 | 1 | −1 | 0.5 | −0.5 |
| 12 | 0 | 0 | 0 | — | 0 | — |
| 13 | 0 | 0 | 0 | — | 0 | — |
| 14 | 0 | 0 | 0 | — | 0 | — |
| 15. Asthenia | | | | | | |
| 1 | 0.5 | 0 | 0 | — | 0 | — |
| 2 | 0.5 | 0 | 1 | −0.5 | 0.5 | — |
| 3 | 0 | 0 | 0.5 | — | 0 | — |
| 4 | 0 | 0 | 1 | −1 | 0 | — |
| 5 | 0 | 0 | 0 | — | 0 | — |
| 6 | 0.5 | 0 | 0 | — | 0 | — |
| 7 | 0 | 0 | 0 | — | 0 | — |
| 8 | 0 | 0 | 0 | — | 0 | — |
| 9 | 0 | 0 | 0 | — | 0 | — |
| 10 | 0 | 0 | 0 | — | 0 | — |
| 11 | 0 | 0 | 0 | — | 0 | — |
| 12 | 1.5 | 0 | 0 | — | 0 | — |
| 13 | 0 | 0 | 0 | — | 0 | — |
| 14 | 0 | 0 | 0 | — | 0 | — |
| 16. Headache | | | | | | |
| 1 | 1 | 0 | 0.5 | — | 0 | — |
| 2 | 1 | 1 | 0 | +1 | 1 | — |
| 3 | 0 | 0 | 0 | — | 0 | — |
| 4 | 2 | 2 | 1 | +1 | 2 | — |
| 5 | 2.5 | 2 | 0 | +2 | 1.5 | +0.5 |
| 6 | 0 | 0.5 | 0 | — | 0.5 | — |
| 7 | 2 | 3 | 0 | +2 | 0 | +2 |
| 8 | 0 | 0 | 0 | — | 0 | — |
| 9 | 0 | 0 | 0 | — | 0 | — |
| 10 | 3 | 1.5 | 0 | −1.5 | 0 | +1.5 |
| 11 | 3 | 2 | 3 | — | 3 | — |
| 12 | 2 | 0 | 0 | — | 0 | — |
| 13 | 0 | 0 | 0 | — | 0 | — |
| 14 | 0 | 0 | 0 | — | 1 | −1 |
| 17. Dizziness | | | | | | |
| 1 | 0 | 2 | 0.5 | — | 0 | — |
| 2 | 1 | 0 | 0 | — | 0 | — |
| 3 | 1.5 | 0.5 | 1 | — | 1.5 | 1 |
| 4 | 1 | 1 | 1 | — | 3 | −2 |
| 5 | 0 | 0 | 0 | — | 2 | −2 |
| 6 | 0 | 0 | 0 | — | 0 | — |
| 7 | 2 | 1 | 0 | +1 | 0 | +1 |
| 8 | 0 | 0 | 0 | — | 0 | — |
| 9 | 1 | 1 | 2 | −1 | 1 | — |
| 10 | 0 | 0 | 0 | — | 0 | — |
| 11 | 0 | 0.5 | 2.5 | −2 | 1 | −0.5 |
| 12 | 3 | 2 | 3 | — | 1 | +1 |
| 13 | 0 | 0 | 0 | — | 0 | — |
| 14 | 0 | 0 | 0 | — | 0 | — |
| 18. Tearfulness | | | | | | |
| 1 | 1 | 1 | 1 | — | 0 | +1 |
| 2 | 2 | 3 | 0 | +2 | 0 | +2 |
| 3 | 0 | 0 | 0 | — | 0 | — |
| 4 | 0 | 0 | 0 | — | 0 | — |
| 5 | 1 | 0 | 0 | 0 | 0 | — |
| 6 | 0 | 0 | 0 | — | 0 | — |
| 7 | 1 | 0 | 0 | — | 0 | — |
| 8 | 0 | 0 | 0 | — | 0 | — |
| 9 | 0 | 0 | 0 | — | 0 | — |
| 10 | 0 | 1 | 0 | — | 0 | — |
| 11 | 0 | 0 | 0 | — | 0 | — |
| 12 | 0 | 0 | 0 | — | 0 | — |
| 13 | 0 | 0 | 0 | — | 0 | — |
| 14 | 0 | 0 | 0 | — | 0 | — |
| 19. Spontaneous activity | | | | | | |
| 1 | 1 | 2.5 | 1.5 | — | 1 | — |
| 2 | 2 | 1 | 1 | — | 1.5 | — |
| 3 | 0.5 | 0.5 | 0.5 | — | 0 | — |
| 4 | 2 | 2 | 2 | — | 1 | +1 |
| 5 | 1 | 1 | 1 | — | 1 | — |
| 6 | 1 | 2 | 1 | — | 1 | 0 |
| 7 | 2 | 1 | 1 | — | 1 | — |
| 8 | 1.5 | 0 | 1 | — | 1 | — |
| 9 | 2 | 2 | 2 | — | 2 | 0 |
| 10 | 0 | 0 | 0 | — | 0 | — |
| 11 | 2 | 2 | 2 | — | 2 | — |
| 12 | 3 | 3 | 3 | — | 4 | −1 |
| 13 | 2 | 1 | 2 | — | 1 | 0 |
| 14 | 0 | 0 | 0 | — | 0 | — |

TABLE 17-continued

Test Results according to E. E. Bukatina et al. Scale

| Patient No. | K1 | K2 | 4 weeks | Changes | 8 weeks | Changes |
|---|---|---|---|---|---|---|
| 20. Elementary self-service | | | | | | |
| 1 | 0 | 0 | 0 | — | 0 | — |
| 2 | 0 | 0 | 0 | — | 0 | — |
| 3 | 0 | 0 | 0 | — | 0 | — |
| 4 | 0 | 0 | 0 | — | 0 | — |
| 5 | 0 | 0 | 0 | — | 0 | — |
| 6 | 0 | 0 | 0 | — | 0 | — |
| 7 | 0 | 0 | 0 | — | 0 | — |
| 8 | 0 | 0 | 0 | — | 0 | — |
| 9 | 1 | 1 | 0 | +1 | 0 | +1 |
| 10 | 0 | 0 | 0 | — | 0 | — |
| 11 | 0 | 0 | 0 | — | 0 | — |
| 12 | 1 | 0.5 | 1 | — | 2 | −1 |
| 13 | 0 | 0 | 0 | — | 0 | — |
| 14 | 0 | 0 | 0 | — | 0 | — |

K1, K2 - examination prior to the treatment: - (—) - improvement (deterioration) of function

*The female patient refused to answer questions

Item 10. No hearing hallucinations were observed throught the whole period of investigations.

Item 11. Visual hallucinations were observed for some days in one female patient (obsrvation 9) on the 4th week of therapy.

Item 12. Senile confusion was observed in one female patient (observation 11) at the beginning of therapy as the arterial pressure went up.

Item 21. Sphincter control was not terminated in a single observation throughout the medical treatment period.

What is claimed is:

1. A method for treating Alzheimer's disease in a patient in need thereof, wherein the method comprises administering to the patient an effective amount of a compound having the formula:

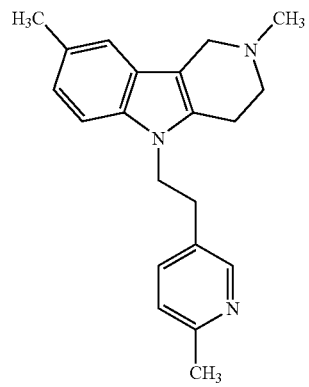

or a pharmaceutically acceptable salt thereof.

2. The method of claim 1, wherein the pharmaceutically acceptable salt is a hydrochloride salt.

3. The method of claim 2, wherein the hydrochloride salt is a dihydrochloride salt.

4. The method of any of claims 1–3, wherein the compound or salt thereof is administered in a pharmaceutical composition.

5. The method of claim 4, wherein the pharmaceutical composition is aqueous.

6. The method of any of claims 1–3, wherein the compound or salt thereof is administered in a tablet.

7. The method of claim 6, wherein the tablet further comprises lactose and magnesium stearate.

8. The method of claim 7, wherein the tablet comprises (a) the compound or salt thereof; (b) lactose; and (c) magnesium stearate in a molecular weight ratio of 1.0:3.0:0.5 compound or salt thereof: lactose:magnesium stearate.

9. The method of any of claims 1–3, wherein the method comprises administering to the patient a thrice daily dose of the compound or pharmaceutically acceptable salt thereof.

10. The method of claim 9, wherein the compound or salt thereof is administered in a tablet.

11. The method of claim 10, wherein the tablet further comprises lactose and magnesium stearate.

12. The method of claim 11, wherein the tablet comprises (a) the compound or salt thereof; (b) lactose; and (c) magnesium stearate in a molecular weight ratio of 1.0:3.0:0.5 compound or salt thereof: lactose:magnesium stearate.

13. The method of any of claims 1–3, wherein the compound or salt thereof is administered orally.

* * * * *